US012109325B2

(12) United States Patent
Link et al.

(10) Patent No.: US 12,109,325 B2
(45) Date of Patent: Oct. 8, 2024

(54) DUCTILE COATING FOR AN IMPLANT COMPONENT

(71) Applicant: WALDEMAR LINK GmbH & Co. KG, Hamburg (DE)

(72) Inventors: Helmut D. Link, Hamburg (DE); Richard Csaszar, Bad Segeberg (DE)

(73) Assignee: WALDEMAR LINK GmbH &Co. KG, Hamburg (DE)

( * ) Notice: Subject to any disclaimer, the term of this patent is extended or adjusted under 35 U.S.C. 154(b) by 533 days.

(21) Appl. No.: 17/606,637

(22) PCT Filed: Apr. 24, 2020

(86) PCT No.: PCT/EP2020/061476
§ 371 (c)(1),
(2) Date: Oct. 26, 2021

(87) PCT Pub. No.: WO2020/216910
PCT Pub. Date: Oct. 29, 2020

(65) Prior Publication Data
US 2022/0233748 A1 Jul. 28, 2022

(30) Foreign Application Priority Data
Apr. 26, 2019 (EP) ..................................... 19171363

(51) Int. Cl.
| | |
|---|---|
| *A61L 27/30* | (2006.01) |
| *A61L 27/42* | (2006.01) |
| *A61L 27/54* | (2006.01) |
| *A61L 31/08* | (2006.01) |
| *A61L 31/12* | (2006.01) |
| *A61L 31/16* | (2006.01) |
| *C22C 14/00* | (2006.01) |
| *C23C 14/02* | (2006.01) |
| *C23C 14/14* | (2006.01) |
| *C23C 14/28* | (2006.01) |

(52) U.S. Cl.
CPC ........... *A61L 27/306* (2013.01); *A61L 27/427* (2013.01); *A61L 27/54* (2013.01); *A61L 31/088* (2013.01); *A61L 31/124* (2013.01); *A61L 31/16* (2013.01); *C22C 14/00* (2013.01); *C23C 14/022* (2013.01); *C23C 14/14* (2013.01); *C23C 14/28* (2013.01); *A61L 2300/104* (2013.01); *A61L 2300/404* (2013.01); *A61L 2420/02* (2013.01); *A61L 2420/04* (2013.01); *A61L 2430/38* (2013.01)

(58) Field of Classification Search
CPC ................. A61F 2/82; A61F 2/30; A61F 2/32
USPC .................................... 424/422, 423; 606/62
See application file for complete search history.

(56) References Cited

U.S. PATENT DOCUMENTS

| | | | |
|---|---|---|---|
| 2009/0076508 A1* | 3/2009 | Weinans | ................. B22C 9/046 606/62 |
| 2009/0198343 A1 | 8/2009 | Spain et al. | |
| 2014/0121759 A1* | 5/2014 | Cully | .................... A61L 31/148 623/1.18 |

FOREIGN PATENT DOCUMENTS

| | | | | | |
|---|---|---|---|---|---|
| CA | | 2623123 C | * | 3/2014 | ............... A61F 2/07 |
| WO | WO 2009/095705 A2 | | | 8/2009 | |
| WO | WO 2015/150186 A1 | | | 10/2015 | |

OTHER PUBLICATIONS

Lin Xiao et al. "Orthopedic implant biomaterials with both osteogenic and anti-infection capacities and associated in vivo evaluation methods," Nanomedicine: Nanotechnology, Biology and Medicine, Elsevier, NL, vol. 13, No. 1, Aug. 20, 2016 (Aug. 20, 2016), pp. 123-142.
Richard Kuehl et al. "Preventing Implant-Associated Infections by Silver Coating" Antimicrobial Agents and Chemotherapy, US, vol. 60, No. 4, Apr. 1, 2016 (Apr. 1, 2016), pp. 2467-2475.
International Search Report and Written Opinion mailed Jul. 30, 2020 in corresponding International Application No. PCT/EP2020/061476 and the English Translation of the International Search Report.

* cited by examiner

*Primary Examiner* — Walter E Webb
(74) *Attorney, Agent, or Firm* — Chiesa Shahinian & Giantomasi PC

(57) ABSTRACT

The invention relates to a coating for an implant component, a method for producing an implant component having said coating, and a use of said coating on an implant component. The coating is intended for an implant component, in particular a spinal implant component, and is a TiNb coating which has, in addition to an atom % proportion of Ti and an atom % proportion of Nb, an atom % proportion of 5-30 atom % of Ag.

13 Claims, No Drawings

DUCTILE COATING FOR AN IMPLANT COMPONENT

CROSS-REFERENCE TO RELATED APPLICATIONS

This application is the National Stage entry under 35 U.S.C. § 371 of International Application No. PCT/EP2020/061476 filed on Apr. 24, 2020, published on Oct. 29, 2020 under Publication Number WO 2020/216910 A1, which claims the benefit of priority under 35 U.S.C. § 119 of European Patent Application Number 19171363.5 filed Apr. 26, 2019, the entireties of which are herein incorporated by reference.

FIELD OF THE INVENTION

The invention relates to an implant component having a TiNb-Ag coating, to a method for the application of this coating and to a use of this coating on an implant.

PRIOR ART

One reason why implants can fail in situ is an infection with pathogens. Such pathogens are predominantly Staphylococci, for example Staphylococcus epidermidis, which colonise the skin and mucous membranes of humans. In addition, the pathogen Staphylococcus epidermidis for example, inter alia, is able to populate an implant surface using a biofilm. This biofilm thus protects a pathogen from antibiotics, phagocytes and other immune responses of the body.

Studies have shown that, for example, Staphylococcus epidermidis is a common cause of postoperative infections after the implantation implants. Upon diagnosis of a postoperative infection, it is generally first attempted to suppress said infection using active substances, for example antibiotics. If this strategy is unsuccessful, it may be necessary to remove the implant. Removing the implant will remove, as far as possible, the source of infection. While this leads to more effective treatment of the infection, it also has the consequence of reducing the patient's mobility.

In the case of an infection with Staphylococcus epidermidis, an additional difficulty is that this microbe regularly has antibiotic resistance (80% according to Takizawa et al. in SPINE Volume 42, No. 7, pp 525-530). According to Takizawa, in the field of spinal surgery there is evidence that the pathogens known as Methicillin-resistant Staphylococcus epidermidis (MRSE) initially exhibit fewer signs of infection due to their low virulence, and therefore carry the risk of an infection only being detected at a late stage. In the worst case, this can lead to higher morbidity for a patient postoperatively than preoperatively, especially if the infection precludes further use of an implant.

In order to avoid such complications, it is therefore desirable to counteract the actual colonisation of pathogens. Thus, US 2009/0198343 A1 proposes providing a coating for an artificial joint, which is intended for the running surfaces of metal pairings, with an antimicrobial effect. In order to achieve this, in US 2009/0198343 A1 a chromium nitride coating is supplemented with silver by the friction surfaces of the implant being alternately coated with chromium nitride and silver. However, chromium nitride is classed as sensitising, and therefore there is a risk after implantation that allergic reactions may occur. In addition, the coating disclosed in US 2009/0198343 A1 is only effective against colonisation by Staphylococcus epidermidis to a very limited extent. In a literature review, Lin Xiao et al. ("Orthopaedic implant biomaterials with both osteogenic and anti-infection capacities and associated in vivo evaluation methods. Nanomedicine: NBM 2017, Vol. 13, pages 123-142, ISSN 1549-9634) compare antibacterial and osteogenic properties of various biomaterials. WO 2015/150186 A1 relates to an implant component having a connecting portion which is at least partially coated with a TiNb coating.

Added to this is the fact that it is desirable, for most implant components, to be able to adapt them by bending before introduction into a patient's body. In other words, these implant components are designed to be plastically deformable, such that they can be adapted to the environment of the implant component or the position of other implant components. These properties are particularly advantageous for rods in the region of the spine and bone plates for treating fractures. However, nitride coatings in particular can only be used for this purpose to a limited extent, as they are not only relatively hard but also relatively brittle. As a result, plastic deformation of an implant component provided with a nitride coating can lead to damage of the coating. Consequently, an increased amount of metal ions, metal oxides, organometallic phosphates and small metal particles can be released and potentially lead to pain, aseptic loosening of the implant component or negative consequences for the surrounding tissue. This can also lead to allergic reactions, which can also necessitate repairing the implant.

SUMMARY OF THE INVENTION

Consequently, it was an object of the present invention to provide a coating for an implant surface which prevents an infection in situ. In particular, it was an object of the invention to provide a coating for an implant surface which counteracts colonisation of pathogens, in particular of Staphylococcus epidermidis. It was also an aim for the coated implant surface not to elicit any allergies or hypersensitivities in the patient. Furthermore, the coated implant surface should be able to withstand any mechanical influences, in particular which arise by the plastic deformation of the implant components, so that an implant component with this coating can be adapted to the anatomical environment of the implantation site.

In light of these objects, the claims define a coating for an implant component, a method for producing an implant component having said coating, and a use of said coating on an implant component.

The coating is intended for an implant component, in particular a spinal implant component, and is a TiNb coating which has, in addition to an atom % proportion of Ti and an atom % proportion of Nb, an atom % proportion of 1-25 atom % of Ag.

The proportion of silver present in this coating is able to prevent an infection caused by pathogens. In this regard, an antimicrobial effect against Staphylococcus epidermidis has in particular been demonstrated. The person skilled in the art can appreciate that the present coating is a coating applied by a technical, machine-based method, which coating is produced during the production of the implant.

Furthermore, the atom % proportion of Ag, i.e. the proportion of silver, in the above-defined range does not lead to any notable reduction in the mechanical resistance of the coating, such that said coating is sufficient for the mechanical contact forces occurring during the implantation. It is believed that the mechanical resistance remains at such a level due to a limited influence of the proportion of silver on ductility. This prevents the implant material or base material of the implant located under the coating from coming into contact with a patient's body tissue and possibly causing hypersensitivity as a result.

Because of its resistance and ductility, the titanium-niobium coating with a proportion of silver, i.e. the TiNb-Ag coating, is particularly suitable for structural implants which support or replace parts of the skeleton when they have been introduced into a patient's body. An example of this is rod-like connecting elements which are used in the region of the spinal column in spinal fusion, in order to fix two vertebrae relative to one another. Such connecting elements are regularly plastically deformed before being fixed in the body, in order to fix the vertebrae relative to one another in a specific position. Because of the ductile properties, the present coating remains intact upon plastic deformation; this therefore prevents alloy constituents from being released into the patient's body which might otherwise lead to hypersensitivities. In other words, essentially no tears or chips occur during coating due to plastic deformation, i.e. the coating also becomes substantially plastic at least to the extent that the coated material of the implant component is sealed in the coated area, even in the deformed state.

The implant component is plastically deformable with the coating. The ductility of the coating is thus preferably the same as, or greater than, the ductility of the material of the implant component. The coating has the property that, as long as a deformation of the implant component to the anatomical environment of an implantation site is plastic, the coating is essentially only plastically deformed. This means that the sealing of the implant component by the coating remains intact by a deformation which is plastic (free of breakage).

It is advantageous here if the coated implant component is not exposed in the patient's body to friction with another implant component due to alternating or swelling loading of the implant components. In other words, there should be essentially no relative movement between the coated implant component and an adjacent implant component, as is for example the case in joint surfaces of a joint replacement.

However, it should be noted that the coating can also advantageously be used in other implant components which are exposed to strong elastic or plastic bending. This includes, for example, bone plates which are used for healing fractures and which, like the abovementioned rod-like connecting elements in the region of the spinal column, are adapted to the anatomical environment by plastic deformation directly before their ultimate implantation. A further example for which the present coating is particularly advantageous is flexible tabs, as are used for example in partial pelvic prostheses. These implant components all have the shared feature that they can be adapted to the anatomical environment of the implantation site by plastic deformation (i.e. a permanent, essentially failure-free deformation). This improves the functionality of such implant components without increasing the costs thereof in the process.

In a preferred embodiment, the coating has 1.5-15 atom % Ag, 1.5-5 atom % Ag or approximately 2 atom % Ag.

These preferred proportions of silver in the coating meet the above requirements. In terms of hardness, the lower the proportion of silver, the greater the hardness. However, a reduction in hardness, as described above, does not substantially affect the resistance and ductility of the coating.

In a further preferred embodiment, the coating has 5-40 atom % Nb, 10-30 atom % Nb, 15-25 atom % Nb or approximately 18 atom % Nb.

These preferred proportions of niobium prevent hypersensitivity reactions in the patient's body and additionally provide the necessary ductility in order to take on essentially no damage under the plastic deformations occurring during an intervention.

As described above, the remaining proportion aside from the Ag proportion and the Nb proportion is substantially taken up by Ti. Substantially refers in this context to the fact that production-related impurities from other compounds may be present, but not exceeding an atom % proportion of 3%, 2% or 1%. In the present coating, Ti preferably has the highest atom % proportion. In particular, the atom % proportion of titanium is preferably 65-90 atom %, 75-85 atom % or approximately 80 atom %.

In one embodiment, Ag and TiNb are formed adjacent to one another on the coating surface.

In this way, the proportion of Ag can better exert its infection-preventing effect. In order to achieve this surface juxtaposition of the coating and thus direct contact with the patient's tissue or fluids, the two coating components are preferably applied simultaneously. This simultaneous application also means that the coating components are additionally substantially uniformly distributed on the implant surface.

In a preferred embodiment, the coating has a thickness of 2.5-6 µm, 3.5-5.5 µm or approximately 4.5 µm.

It has been determined that these coating thicknesses prevent at least continuous damage to the coating. Here, a thicker coating tends to be advantageous. A thickness beyond these values, on the other hand, does not afford any particular improvements but rather may promote inhomogeneity and delamination of the coating. It is believed that the mechanical resistance of the coating at the indicated thicknesses is also due to the fact that there are no continuous portions of silver in the thickness direction. In other words, the three-dimensional heterogeneous structure of the TiNb-Ag coating means that there is an in principle continuous TiNb coating.

In one embodiment, the TiNb coating is substantially present as a non-stoichiometric TiNb layer.

Such a layer forms, together with the proportion of silver, a particularly uniform inert layer with an antimicrobial effect and thereby, after implantation of the implant, acts effectively against both hypersensitivity and infection.

An implant component, in particular of a spinal implant, is furthermore provided, which is at least partially coated with a coating according to one of the above embodiments.

As described above, infections can occur in particular due to the implant being exposed to the environment prior to implantation. In this regard, it was possible to determine that particularly in the region of the spinal column such infections are commonly attributable to the pathogen Staphylococcus epidermidis. As a result, the preventative action of a coating according to the invention is particularly effective here.

It should be emphasised that the displacements of the coating structure caused by bending have essentially no effect on the infection-inhibiting effect of the coating.

In a preferred embodiment, the implant component is a component of a spinal fusion implant and in particular a connecting rod of such a spinal fusion implant.

In the case of a spinal fusion implant, connecting rods which connect at least two vertebrae for stiffening are particularly preferably provided with the present coating.

In a particularly preferred embodiment, the surface of the coated portion has TiNb with Ag islands embedded therein.

As described above, such a distribution of TiNb and silver in the coating makes it possible to produce a substantially continuous TiNb coating, since the embedded Ag islands generally do not extend through the entire coating thickness. This achieves sufficient mechanical resistance or hardness of such a coating, since TiNb has a greater hardness in the coating than Ag.

In a further preferred embodiment, the implant component to be coated has a titanium alloy and preferably consists of said titanium alloy.

Firstly, the TiNb-Ag coating, because of the TiNb proportion, adheres particularly well to a titanium alloy of such an implant component, thereby preventing detachment of the coating. Secondly, an implant component to be coated, made of a titanium alloy, further reduces the risk of hypersensitivity, since such hypersensitivity is improbable, even in the event of damage to the coating, due to the biocompatibility of titanium. The adhesion of the coating can be further improved in this embodiment by applying a coating containing essentially only Ti as a sort of adhesion-promoting coating before the TiNb-Ag coating.

A method for producing an implant component with a coating as described above is also provided, which method comprises the steps of providing an implant component to be coated in a coating chamber, in particular an implant component for a spinal implant; providing at least one target, such that upon evaporation a predetermined atom % ratio of titanium, niobium and silver is produced; providing an inert atmosphere; evaporating the at least one target; and simultaneously coating the implant component with the evaporated metal of the at least one target.

This method enables simultaneous coating with titanium, niobium and silver in order to form the TiNb-Ag coating. The simultaneous coating ensures that silver is exposed at the surface of the coating and as a result, in the implanted state, the implant component can exert the infection-inhibiting effect of the coating. In addition, by selecting the number of the respective targets of the coating components, the atom % proportion of the coating components can be adjusted, at least in its order of magnitude, to the desired composition of the coating. Here, the atom % ratio of the coating components produced during the evaporation substantially corresponds to the desired atom % ratio of the coating applied to the implant components.

Alternatively or in addition to adjusting the composition of the coating by the number of respective targets, at least one target can be provided which has a specific ratio of titanium and silver. Preferably, however, use is exclusively made of one or more such targets with specific atom % proportions of titanium, niobium and preferably silver corresponding to the desired composition of the coating.

In a preferred embodiment, the at least one target is evaporated by means of arc evaporation. In the process, the voltage applied to the target is 15-30 V or 20-25 V and the current applied is 40-70 A.

These setting ranges for the voltage and the current make possible, just like the abovementioned number of targets of the respective coating components, the possibility of adjusting the coating composition. In particular, the ratio arrived at by the choice of the number of targets can be adjusted even more finely.

In a further embodiment, after providing the implant to be coated in the coating chamber, the implant surface to be coated is purified by glow discharge under a hydrogen atmosphere.

This purification step has the advantage of removing any organic residue which may be present on the surface of the implant to be coated, thereby improving the adhesion of the coating to the implant.

In one embodiment, after introducing the implant to be coated into the coating chamber, the implant surface to be coated is purified by bombarding the implant surface with high-energy ions under an inert atmosphere.

As a result, an oxide layer present on the surface of the implant is removed, which would otherwise reduce the adhesion of the coating to the implant.

Such an oxide layer is formed for example on implants made of titanium alloys and can be removed in particular by bombarding with argon and titanium ions by the method step of this embodiment. Here, the titanium ions can preferably be produced by a Ti target which is to be used for the coating. The inert atmosphere here, for example an argon atmosphere, counteracts renewed formation of an oxide layer.

In a particular embodiment of the production method, said method further comprises the step of plastically deforming the coated implant component before implantation.

This plastic deformation makes it possible to prepare the now coated implant components for, and before, introduction into the patient's body in terms of the shape thereof.

Furthermore, a use of the above-described coating for preventing a biofilm on an implant, in particular a spinal implant, is provided.

Such a use of the coating is, as already described above, particularly advantageous.

DETAILED DESCRIPTION OF PREFERRED EMBODIMENTS

As mentioned above, a coating in the context of the present invention is to be understood to mean a coating applied by a technical method. Examples of such technical methods are chemical vapour deposition (CVD), physical vapour deposition (PVD) or galvanic coating methods.

As described above, a coating according to the invention comprises a mixture of a titanium-niobium coating into which silver is incorporated (TiNb-Ag coating). In other words, the coating has at least an individual layer of a titanium-niobium coating in which silver is embedded. Here, the silver is particularly present in the form of silver islands, i.e. silver or silver atoms are arranged next to the TiNb lattice.

Because of the size of the silver atoms, it is assumed that only a small proportion, if any, of the silver is arranged interstitially within the TiNb lattice. Rather, it was observed that the silver is present in the TiNb-Ag coating in the form of silver agglomerates. In other words, the silver is substantially not integrated in the TiNb lattice. The silver agglomerates are preferably present at a size in a range from 1 µm to 50 µm and more preferably in a range from 5 µm to 30 µm.

Furthermore, it is assumed that the efficacy of the silver arises in particular from the fact that the silver, in the implanted state of the implant component, transforms to the ionic state upon contact with bodily fluids by local element formation, and thus exerts its antimicrobial effect. This local element formation is made possible by the above-described arrangement of the silver islands (Ag islands) on the surface of the coating. This arrangement is achieved by simultaneous coating of the implant with titanium, niobium and silver.

The coating, because of its antimicrobial properties, has an infection-inhibiting effect which relates in particular to Staphylococcus epidermidis. It is believed that the proportion of silver of the coating present in the TiNb matrix disrupts the formation of a biofilm grown by these bacteria. Due to this disruption, the protective mechanism of the bacteria against antibiotics brought about by this biofilm at least no longer functions sufficiently, and therefore they can be suppressed.

Further, it was observed that the silver can dissolve from the coating in the form of ions. It is assumed that these silver particles ionised at the surface of the coating form an active zone (inhibition zone) in the immediate environment of the implant, where they exert their antimicrobial effect. Consequently, the coating can be used to prevent not only infection spreading directly from the surface of the implant, but also those that would otherwise develop in the surroundings of the implant component.

A TiNb-Ag coating with a proportion of silver of 5-30 atom % exerts an antimicrobial effect. This is particularly effective against Staphylococcus epidermidis. As described above, this pathogen can usually be found on human skin and presumably as a result of this is a frequent cause of infections arising after the implantation. Studies indicate that there is an increased risk of this pathogen causing a serious infection after implantation, especially in the spinal region. This is possibly favoured by the fact that Staphylococcus epidermidis has comparatively low virulence among the Staphylococci. This leads to signs of infection only appearing at a late stage, and possibly being overlooked at earlier stages. Since the coating has an inhibitory effect particularly against this pathogen, it is possible in particular for the reason mentioned above to prevent infections which are only detected at a late stage.

Preferably, the atom % proportion of silver and/or the atom % proportion of niobium are each smaller than the atom % proportion of titanium. In other words, it is not necessary for a stoichiometric distribution to be present. The distribution of the coating components can be superstoichiometric or substoichiometric. In total, the coating has a proportion of at least 80 atom %, and in particular at least 90 atom %, of TiNb. The atom % proportion of titanium is preferably 65-90 atom %, 75-85 atom % or approximately 80 atom %.

A maximum proportion of silver of 25 atom % ensures that the TiNb has deposits of silver, or silver islands, and not the other way around. This has the advantage of the TiNb being provided as a substantially continuous coating in which the silver is embedded. As described above, as a result there are preferably no regions on the coating where a silver island extends completely through the thickness of the coating. The silver dissolving out therefore has essentially no negative impact on the functionality and integrity of the coating.

Other preferred proportions of silver for the present coating, for example a proportion of silver of 1.5-15 atom %, 1.5-5 atom % or approximately 2 atom %, also have this advantage. This structure of the coating leads, inter alia, to at least a part of the proportion of silver being present next to the TiNb proportion on the coating surface, in particular in the coating method described below.

The proportion of silver, together with the TiNb proportion as TiNb-Ag coating, in addition to the abovementioned antimicrobial effect, also gives rise to no substantial change in the mechanical properties in relation to a pure TiNb coating. Thus, it still has sufficiently high hardness to prevent damage during handling of the implant during implantation, and at the same time sufficient ductility which essentially does not damage the integrity of the coating upon elastic or plastic deformation of the implant. As a result, the TiNb-Ag coating protects both against infection and at least excessive release of alloy components which otherwise have the potential to elicit hypersensitivity in patients.

It is believed that not only the hardness but also the ductility supports the mechanical resistance or strength of the coating, such that it withstands mechanical influences arising during an implantation of the implant component. Such mechanical influences occur, for example, when creating a press fit of an implant component in the bone tissue, through contact of an implant component with a fastening element, for example when screwing in bone screws for fastening a plate or a clamp, or in particular a plastic deformation of the implant component. In the area of the spine, such loads occur, for example, during the assembly of implant components, such as a spinal fusion construct. Also in the treatment of fractures, such loads acting on the implant component occur during implantation.

For these reasons, the present coating is particularly suitable for implant components which, after implantation, support a patient's skeleton or replace parts of this skeleton. For such implant components, mechanical loading of the coating generally occurs during implantation and assembly of an implant. After implantation, stresses and strains occur in the coating of an implant component, particularly as a result of the everyday loading of the implant in a patient's body. The present coating can also withstand such stresses and strains.

In other words, the coating is above all suitable for implant components in which friction occurs predominantly during the implantation and/or assembly of the implant and the coating in the implanted state experiences essentially no functionally caused friction. It was determined that, for this purpose, a thickness of the coating of less than 10 μm, in particular of 2.5-6 μm, preferably 3.5-5.5 μm and more preferably of approximately 4.5 μm, is sufficient. It is nonetheless conceivable to also use such a coating with a greater layer thickness.

Furthermore, in the present coating, the difference in the material properties, in particular the elasticity, to the underlying base material of the implant can be partially reduced by the proportion of silver. This also enables sufficient mechanical resistance and adhesion of the coating. Also, for this reason inter alia, the coating can be applied to a wide variety of different implant materials including not only metal alloys but also polymers, for example polyethylene or PEEK. The present coating can thus improve in particular the resistance of implant components produced from a polymer.

In summary, the TiNb-Ag coating therefore exhibits both advantageous antimicrobial properties and advantageous mechanical properties which can be of great use for the patient for an implant or implant component at least partially coated with this coating.

As has already been described above, such a coating is produced in particular by methods with physical vapour deposition (PVD methods).

To this end, the implant component to be provided with the coating is purified, preferably with water, before being introduced into the coating chamber.

The implant is placed in the coating chamber which is subsequently evacuated. For the subsequent process, the implant is preferably heated to 400 to 600° C. in order to improve the mobility of ions at the surface of the implant and achieve better adhesion of the coating on the implant.

The surface of the implant component is preferably purified in the coating chamber before applying the coating. For example, a purification by glow discharge under a hydrogen atmosphere may be carried out in order to remove any organic residues on the uncoated implant surface.

It is furthermore possible to purify the surface of the implant component by means of ion etching. Here, the implant component is bombarded with ions (for example titanium ions or argon ions) under an inert atmosphere, in particular an argon atmosphere, in order to remove an oxide layer present at the surface of the uncoated implant material. This also achieves better adhesion of the coating to the surface of the implant.

Each of the abovementioned purification steps takes place preferably at a negative pressure atmosphere of $10^{-1}$ to $10^{-4}$ mbar.

After the optional purification by at least one of the above-described purification steps, the coating is applied to the implant component, also under an inert atmosphere, in particular an argon atmosphere.

As has already been described, this coating can be produced according to its desired composition with at least one silver target, at least one niobium target and at least one titanium target. It is equally possible to use one or more targets which have the atom % proportions of titanium, niobium and/or silver intended for the coating. In other words, targets which consist of at least two of the coating components, in particular of the intended atom % proportions of titanium and silver, can be used. Consequently, the composition of the coating is at least partly determined by the composition of the target.

In order to keep scattering of the evaporated target material on gas particles in the coating chamber and thus the loss of target material as low as possible, the coating is carried out under a negative pressure in a range of $10^{-1}$ to $10^{-3}$ mbar.

Once the desired atmosphere is set, the process of evaporating the at least one target begins. Particularly preferably, an arc is used for this purpose, which dissolves material from the targets by means of a strong current by means of electrical discharge and transfers it into the gas phase. For this discharge, in particular voltages in a range of 15-30 V and preferably in a range of 20-25 V, and currents in a range of 40-70 A are used. However, it is understood by the person skilled in the art that other processes can also be used to evaporate the targets, such as thermal evaporation, electron beam evaporation or laser beam evaporation.

At least during part of the coating process, even when using several targets made of different materials, the coating with these targets is carried out simultaneously in order to create the island-like structure of the TiNb-Ag coating described above.

Depending on the base material of the implant to be coated, a negative voltage of 100 V to 1500 V can also be applied to it in order to improve adhesion and layer homogeneity. The targets and the implant can also be moved relative to each other during the coating process in order to achieve as uniform a coating as possible.

After coating and a cooling phase, the coating chamber is ventilated again, and the coated implant(s) can be removed. The cooling is preferably carried out with the support of a gas atmosphere (e.g. nitrogen or an inert gas) for improved heat dissipation, which therefore accelerates the cooling process.

The invention claimed is:

1. An implant component which is at least partially coated with a coating, comprising a TiNb coating having an atomic percent of Ti and an atomic percent of Nb, and an atomic percent of Ag, wherein the atomic percent of Ag is from 1-25 percent, and the implant component is plastically deformable.

2. The implant component according to claim 1, wherein the coating has 1.5-15 atomic percent Ag, 1.5-5 atomic percent Ag, or approximately 2 atomic percent Ag.

3. The implant component according to claim 1, wherein the coating has 5-40 atomic percent Nb, 10-30 atomic percent Nb, 15-25 atomic percent Nb or approximately 18 atomic percent Nb.

4. The implant component according to claim 1, wherein Ag and TiNb are formed adjacent to one another on the coating surface.

5. The implant component according to claim 1, wherein the coating has a thickness of 2.5-6 µm, 3.5-5.5 µm or approximately 4.5 µm.

6. The implant component according to claim 1, wherein the TiNb coating is substantially present as a non-stoichiometric TiNb layer.

7. The implant component according to claim 1, wherein the implant component is a bone plate or a spinal implant component.

8. The implant component according to claim 1, wherein the surface of the coated portion has TiNb with Ag islands therein.

9. The implant component according to claim 1, wherein the implant component to be coated comprises a titanium.

10. A method for producing an implant component, wherein the method comprises the steps of:
   providing an implant component to be coated in a coating chamber;
   providing at least one target, such that upon evaporation a predetermined atomic percent ratio of titanium, niobium and silver is produced;
   providing an inert atmosphere;
   evaporating the at least one target
   simultaneously coating the implant component with the evaporated metal of the at least one target; and
   plastically deforming the coated implant component before implantation.

11. The method according to claim 10, wherein the at least one target is evaporated by means of arc evaporation and the voltage applied to the target is 15-30 V or 20-25 V and the current applied is 40-70 A.

12. The method according to claim 10, wherein, after providing the implant to be coated in the coating chamber, the implant surface to be coated is purified by glow discharge under a hydrogen atmosphere.

13. The method according to claim 10, wherein, after introducing the implant to be coated into the coating chamber, the implant surface to be coated is purified by bombarding the implant surface with ions under an inert atmosphere.

* * * * *